US00PP35897P3

(12) United States Plant Patent
Clark et al.

(10) Patent No.: US PP35,897 P3
(45) Date of Patent: Jul. 2, 2024

(54) NECTARINE TREE NAMED 'A-783CN'

(50) Latin Name: *Prunus persica*
Varietal Denomination: A-783CN

(71) Applicant: THE BOARD OF TRUSTEES OF THE UNIVERSITY OF ARKANSAS, Little Rock, AR (US)

(72) Inventors: John R. Clark, Fayetteville, AR (US); Margaret Worthington, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 67 days.

(21) Appl. No.: 17/968,494

(22) Filed: Oct. 18, 2022

(65) Prior Publication Data

US 2024/0130260 P1 Apr. 18, 2024

(51) Int. Cl.
*A01H 5/08* (2018.01)
*A01H 6/74* (2018.01)

(52) U.S. Cl.
USPC ..... Plt./188
CPC ..... *A01H 6/7454* (2018.05); *A01H 5/08* (2013.01)

(58) Field of Classification Search
USPC ..... Plt./188
CPC ..... A01H 5/08; A01H 5/00; A01H 6/7454; A01H 6/74
See application file for complete search history.

(56) References Cited

U.S. PATENT DOCUMENTS

| | | | |
|---|---|---|---|
| PP12,620 P2 | 5/2002 | Clark et al. | |
| PP12,622 P2 | 5/2002 | Clark et al. | |
| PP12,641 P2 | 5/2002 | Clark et al. | |
| PP15,159 P3 | 9/2004 | Clark | |
| PP17,742 P3 | 5/2007 | Clark | |
| PP17,911 P3 | 8/2007 | Clark | |
| PP22,464 P3 | 1/2012 | Clark | |
| PP26,367 P3 | 2/2016 | Clark et al. | |
| PP26,402 P3 | 2/2016 | Clark et al. | |
| PP26,920 P3 | 7/2016 | Clark | |
| PP31,192 P2 * | 12/2019 | Worthington | A01H 5/08 Plt./188 |

OTHER PUBLICATIONS

Beckman, T. G., et al. "Peach tree short life." Southeastern peach growers handbook. University of Georgia, College of Agricultural and Environmental Sciences. Cooperative Extension Service, Athens (2004): 199-205.
Clark, J. R., et al. "'White Diamond' and 'White Cloud' Peaches." HortScience 46.4 (2011): 665-667.
Clark, J. R., et al. "White River Peach." HortScience 38.6 (2003): 1257-1259.
Clark, J. R., et al. "'Souvenirs' Peach." HortScience 48.6 (2013): 800-803.
Clark, J. R., et al. "'White Rock' and 'White County' peaches." HortScience 40.5 (2005): 1561-1565.
Ghiani, A., et al. "Melting of 'Big Top' nectarine fruit: Some physiological, biochemical, and molecular aspects." Journal of the American Society for Horticultural Science 136.1 (2011): 61-68.
Plant Variety Protection 9400013. Peach BY520-9. Issued Jun. 14, 2001. 34 pp.
Sandefur, P. et al. "Peach texture." Horticultural Reviews vol. 41 (2013): 241-301.
University of Arkansas Division of Agriculture Research & Extension. Whitewater Peach flyer. Jan. 2021. Available online at https://cpb-us-e1.wpmucdn.com/wordpressua.uark.edu/dist/3/599/files/2021/01/Whitewater-release-flyer.pdf, one page.
Vauterin, L., et al. "Reclassification of xanthomonas." International Journal of Systematic and Evolutionary Microbiology 45.3 (1995): 472-489.
Worthington, M. and Clark, J.R. Peach breeding at the University of Arkansas. Acta Hortic. (2021). 1304, 21-28.
Clark, J.R. et al. 'Bowden' and 'Amoore Sweet' nectarines. HortScience (2013) 48(6):804-807.

* cited by examiner

*Primary Examiner* — June Hwu
(74) *Attorney, Agent, or Firm* — Quarles & Brady, LLP

(57) ABSTRACT

Description and specification of a new and distinct nectarine tree cultivar named 'A-783CN' which originated from a hand-pollinated cross of 'A-699N' nectarine (female parent) x 'A-717' peach (male parent) in 2004. This new nectarine cultivar can be distinguished by its white, mid-acid, non-melting flesh, mid-season ripening, medium size, attractive appearance, and resistance to bacterial spot disease.

3 Drawing Sheets

Latin name: *Prunus persica.*
Varietal denomination: 'A-783CN'.

BACKGROUND

A new and distinct nectarine tree named 'A-783CN' is described herein. The new cultivar originated from a hand-pollinated cross of A-699N nectarine (female parent; a non-patented, unreleased breeding selection) x A-717 peach (male parent; a non-patented, unreleased breeding selection) made in 2004 near Clarksville, AR. This new cultivar was selected in 2006 for its potential as a fresh-market nectarine in Arkansas and the mid- to upper-southern United States. 'A-783CN' can be distinguished by its white, mid-acid, non-melting flesh, mid-season ripening, medium size, attractive appearance, and resistance to bacterial spot disease.

SUMMARY OF THE INVENTION

The new and distinct nectarine cultivar originated from a hand-pollinated cross of A-699N nectarine (female parent) x A-717 peach (male parent) made in 2004 near Clarksville, AR. The seeds resulting from this controlled hybridization were germinated in a greenhouse in late winter 2004 and planted in a field near Clarksville, AR. The seedlings fruited during the summer of 2006 and one seedling, designated 'A-783CN', was selected for its non-melting flesh, mid-season ripening, attractive appearance, excellent white peach flavor, and resistance to bacterial spot disease.

During 2008, the original plant selection was propagated asexually, at the above-noted location, by budding onto standard peach rootstock cultivar 'Guardian'® (BY520-9; U.S. Plant Variety Protection No. 9,400,013) and a test plot of two plants was established. During asexual multiplication, the characteristics of the original plant have been maintained and no aberrant phenotypes have appeared.

BRIEF DESCRIPTION OF THE PHOTOGRAPHS

The accompanying photographs show typical specimens of the new cultivar in color as nearly true as it is reasonably possible to make in a color illustration of this character.

DETAILED DESCRIPTION OF THE NEW CULTIVAR

Figure 1:
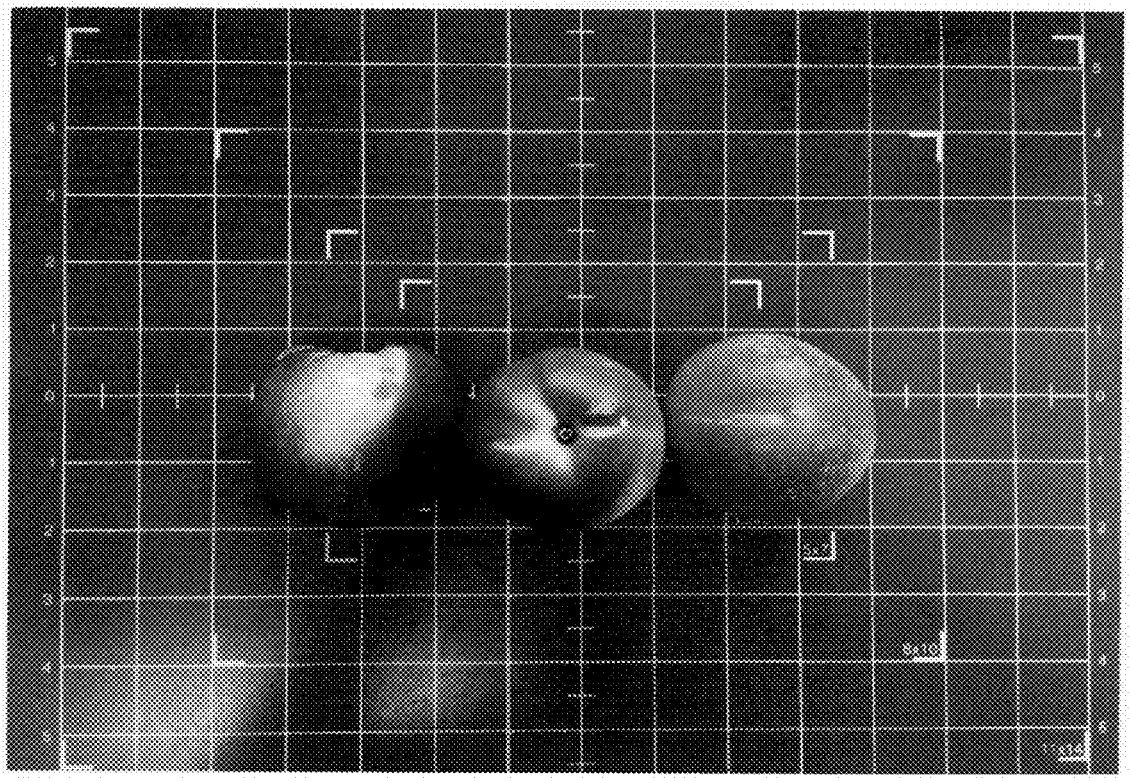
FIG. 1 is a photograph of mature fruit from an 'A-783CN' tree at twelve years of age.
Figure 2:
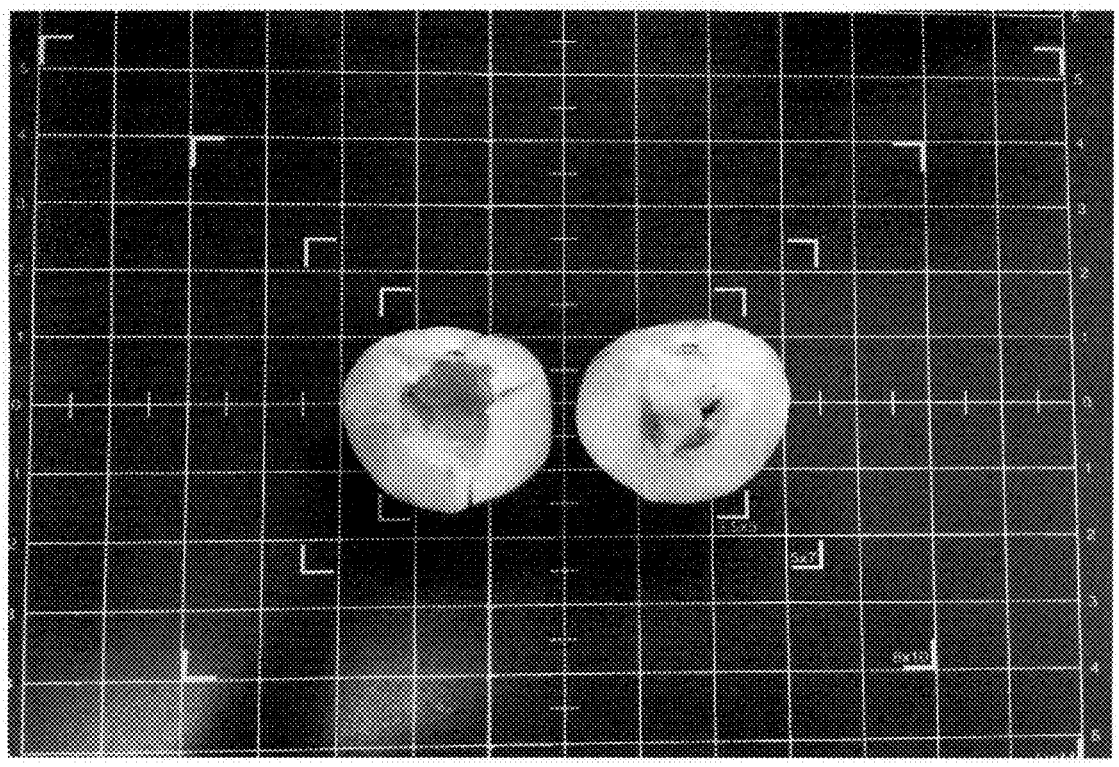
FIG. 2 is a photograph of a longitudinally cut mature fruit from a 'A-783CN' tree at twelve years of age.
Figure 3:
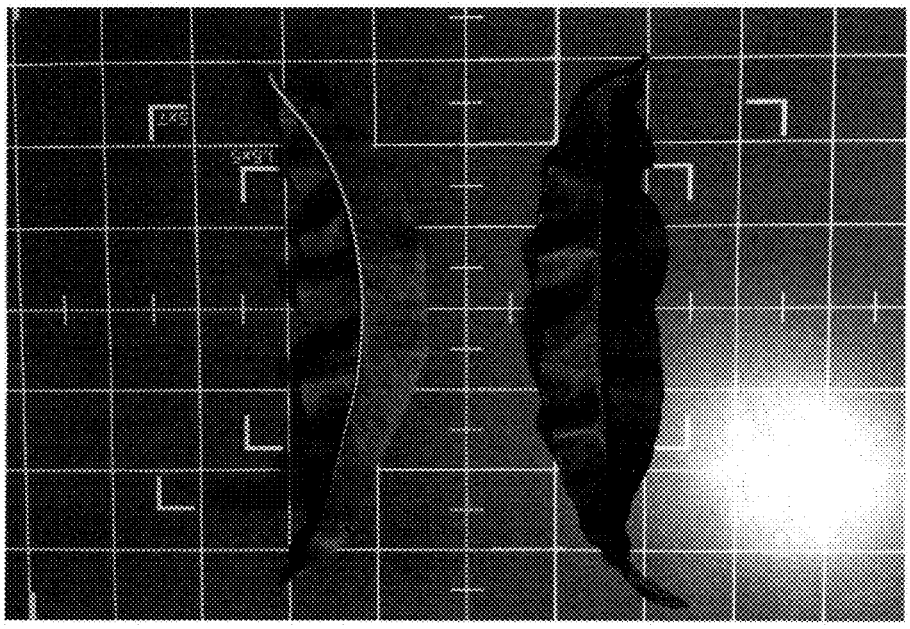
FIG. 3 is a photograph of the abaxial (left) and adaxial (right) sides of mature 'A-783CN' leaves collected from a tree at twelve years of age.

Plants and fruit of this new cultivar are similar to its parents. 'A-783CN' and both of its parents, 'A-699N' and 'A-717', have white flesh. 'A-783CN' is a mid-acid nectarine, but one parent, 'A-699N' is a low-acid nectarine and the other parent, 'A-717', is a high-acid peach. Both parents are early-season ripening, while 'A-783CN' is mid-season ripening. Both the parents and the new cultivar are the genus and species *Prunus persica*.

Trees of the new cultivar are vigorous, productive, standard in size, well- branched and symmetrical with a semi-upright growth habit, comparable to other peach trees. Trees express a moderate level of resistance to both foliar and fruit infection of bacterial spot [*Xanthomonas campestris* pv. *pruni* (Smith) Dye]. The new cultivar blooms in the spring on approximately the same date as 'Bradley' (U.S. Plant Pat. No. 12,620), 'Effie' (U.S. Plant Pat. No. 31,192), and 'Westbrook' (U.S. Plant Pat. No. 12,622). No winter cold injury was observed on wood or buds of the new cultivar in Arkansas tests in years where minimum temperatures have reached 2° F. (−17° C.) during evaluation. However, moderate bud damage was observed in spring 2021 after low temperatures reached −15° F. (−26° C.) in February 2021. Chilling requirement to break dormancy is estimated to be 800 hours below 45° F. (7° C.).

Fruit of the new cultivar ripens mid-season which is very similar to 'Amoore Sweet' (U.S. Plant Pat. No. 26,367) and 'Bowden' (U.S. Plant Pat. No. 26,402) and averages 5-10 days before 'Effie' (U.S. Pat. No. 31,192). Ripening date varied widely across years for all cultivars, with the first harvest date of 'A-783CN' ranging from 18 June in 2017 to 22 July in 2013 in west-central Arkansas (Clarksville). Yield of the new cultivar has not been evaluated, as this new plant is intended for the home gardening market. However, 'A-783CN' has been generally noted to have good productivity.

The fruit is medium oblate in shape. Fruits are attractive with an average 78% bright red blush. The average firmness rating of 'A-783CN' was 8.3, which was comparable to 'Effie'. The flesh of the fruit is white in color with no red flecking or discoloration. Flesh is of the non-melting type and is very firm at maturity. Fruit size is medium, averaging 175 g, slightly more than 'Bradley', 'Amoore Sweet', 'Bowden', and 'Effie'. The fresh fruit has excellent white nectarine flavor and was rated highly in evaluations. Fruits average 13.0% soluble solids, higher than 'Bradley' and 'Westbrook', but lower than 'Effie', 'Bowden', and 'Amoore Sweet'. The flavor is sweet with medium acidity. The titratable acidity level of 'A-783CN' was 0.41% malic acid, which was similar to 'Effie' with 0.44%, higher than 'Amoore Sweet' with 0.22%, and lower than 'Bowden' with 0.64%.

The following is a detailed description of the botanical and pomological characteristics of the subject nectarine. Color data are presented in Royal Horticultural Society Colour Chart designations (2015 $6^{nd}$ edition). Where dimensions, sizes, colors and other characteristics are given, it is to be understood that such characteristics are approximations of averages set forth as accurately as practical.

Plants used for botanical data were twelve years old and grown on a fine sandy loam soil with trickle irrigation near Clarksville, AR. Trees were trained to an open-center training system and dormant pruned annually. The exception to this is that yield data was collected on trees four years old and trained to a perpendicular V training system. Fruits on all trees were thinned to approximately 6-8 inches between fruits 4-5 weeks after full bloom. The trees were fertilized near budbreak (late March on average) with complete or nitrogen fertilizer. Weeds were controlled with pre- and postemergence herbicides. Routine commercial fungicide and insecticide applications were made to the trees, but no bactericides (for control of bacterial diseases such as bacterial spot disease) were applied. The descriptions reported herein are from specimens grown near Clarksville, AR.

Plant:

*Size*.—Mature trees (twelve years of age) average 3.6 m to 3.8 m in height and 4.8 to 5.9 m in spread or width, and a semi-upright growth habit, as grown on 'Guardian® BY520-9' rootstock using an open-center training system commonly used on peaches. Tree size is comparable to that of the 'Amoore Sweet' and 'Bowden' cultivars.

*Growth*.—Vigorous, symmetrical form, good canopy development. Vigor comparable to that of the 'Amoore Sweet' and 'Bowden' cultivars.

*Productivity*.—Good productivity and consistent from year to year. Crop load ratings averaged 6.4 on a 10-point scale. These ratings were comparable to those for 'Westbrook' and 'Bradley'. Yield has not been evaluated.

*Cold hardiness*.—Wood hardy to −15° F. (−26° C.), the coldest temperature that the trees were exposed to at the test site, but hardiness may exceed this temperature. Dormant buds hardy to 2 20 F. (−17° C.), but moderate damage and reduced bloom density were observed following −15° F. (−26° C.) temperatures in February, 2021.

*Disease resistance*.—Leaves and fruit resistant but not immune to bacterial spot under growing conditions where bacterial spot infection is often very severe on susceptible genotypes. No bactericides were used in the development or evaluation of the instant cultivar. The average severity rating for leaf symptoms on 'A-783CN' observational trees was 2.2 out of 5, which was comparable to 'Westbrook'. A commercial fungicide program was followed in orchards used in the development and evaluation of the instant cultivar, thus no resistance to brown rot (*Monilinia fructicola* (G. Winter) Honey) or scab (*Fusicladium carpophilum* (Thum.) Oudem), the other common diseases at Clarksville, AR, were determined.

*Insect resistance*.—Insecticides were applied to orchards used in the development of the instant cultivar to control the common insects at the location including oriental fruit moth (*Grapholita molesta* (Busck)), plum curculio (*Conotrachelus nenuphar* (Herbst)), stinkbug (*Halyomorpha halys* (Stat); *Euschistus servers* (Say); *Acmsternum hilare* (Say); *Nezara viridula* (Linnaeus); *Thyanta* spp.), tarnished plant bug (*Lygus lineolaris* (Palisot de Beauvois)), lesser peach tree borer (*Synanthedon pictipes* (Grote & Robinson)), and greater peach tree borer (*Synanthedon exitiosa* (Say)). Therefore, no insect resistance was determined in the testing of the instant cultivar.

Foliage/shoots/branches:

*Shoots*.—Texture: smooth; dormant-season shoot (branch): length 70.7 cm; diameter at base: 0.7 cm; diameter at midpoint: 0.5 cm; diameter at terminal: 0.3 cm; internode length at base: 5.4 cm; internode length at midpoint: 3.4 cm; internode length at terminus: 2.4 cm; dormant-season shoot color: greyed-orange group (165B) where shaded; greyed-purple group (183A) where exposed to sun; shoot apex color: greyed-purple group (183A).

*Leaves*.—Simple, alternate, glabrous, lanceolate, petiolate, and deciduous, Venation pinnate; base acute; terminal or apex acuminate; margin serrated. Mature leaf size: length 14.2 cm; width at midpoint: 3.5 cm. Leaf serrations: 5 per cm. Mature leaf color: abaxial-Green Group (137C); adaxial — Green Group (137A). Young leaf color: abaxial — Yellow-Green Group (144A); adaxial — Yellow-Green Group (144B); anthocyanin not present on abaxial or adaxial surface of young leaves on midrib or other location. Petiole length mature leaf: 10.1 mm; petiole width: 1.8 mm; petiole texture: smooth no pubescence; petiole strength: moderate; petiole color abaxial: Yellow-Green Group (144B); petiole color adaxial: Yellow-Green Group (144A). Nectaries — shape: globose; number: 2 per leaf; located at base of leaf blade at top of petiole; length: 0.12 cm; width: 0.10 cm; color: Yellow-Green Group (145B). Stipules — length: 4.1 mm; width: 1.6 mm; texture: smooth, no pubescence; color abaxial: Green Group (143C); color adaxial: Green Group (143B); length of leaf blade tip: 2.79 mm; leaf shape in cross section: flat to mildly concave.

*Buds* (*vegetative*).—Number of buds per 15 cm: 7.2, evenly distributed along the shoot; bud length: 4.8 mm; bud diameter: 1.5 mm; shape of bud apex: acute; overall shape: ovate; texture: dense pubescence; position relative to one-year-old shoot: adpressed to slightly held-out; bud shelf length: 3.3 mm; bud shelf width: 3.7 mm; color of bud apex: Greyed-Green Group (198D).

Bark (of mature trunk of tree):

*Color*.—Greyed-Green Group (198C) (at 50 cm above soil level).

*Texture*.—Rough; pubescence absent; lenticel density: 5 per $cm^2$; lenticel color: Greyed-Orange Group (164B).

*Trunk diameter*.—11.6 cm (at 25 cm above ground level).

Flowers: Bloom occurs prior to vegetative bud break; solitary to occasional double individual flowers at a single node; perfect; self fertile.

*Buds* (*floral*).—Number of floral buds 15 cm from terminus: 11.8; dormant bud length: 0.7 cm; diameter: 0.3 cm; color: Greyed-Green Group (197B); shape: oval; texture: dense pubescence on bud scales that lighten nearest the pedicel.

*Date of bloom*.—First, Julian 75 (March 16); Full, Julian 80 (March 21).

*Size* (*fully open*).—Diameter: 2.3 cm; depth: 1.8 cm.

*Type*.—Non-showy (campanulate).

*Color*.—Abaxial margin: Red Group (55B); abaxial center: Red Group (49D); adaxial margin: Red Group (55C); adaxial center: Red Group (49D).

*Sepals*.—Number: 5; length: 5.9 mm; width: 3.9; overall shape: ovate; apex shape: rounded; base shape: truncate; margin: entire; adaxial color: Green Group (142A); abaxial color: Yellow-Green Group (145A).

*Petals*.—Number per flower: 5; shape overall: medium elliptic; shape at apex: obtuse; shape at base: acuminate; margin: sinuate; length: 11.4 mm; width: 9.1 mm; texture: smooth on both the abaxial and adaxial surfaces; petal arrangement: free to slightly overlapping.

*Pistil*.—Length: 1.3 cm; stigma color: Yellow-Green Group (151A); style color: Yellow-Green Group (150C); stigma position relative to anthers: stigma is nearly even in length with and mostly parallel with anthers.

*Stamens*.—Average 44.4 per flower with pollen present, fertile and abundant; pollen color: Yellow-Green Group (151A); stamen and anther position relative to petals: anthers are even with to slightly longer than petals and run perpendicular with petals; stamens are parallel with petals.

*Ovary*.—Texture: smooth; color: Yellow-Green Group (151B).

Fruit:

*Size*.—Medium, avg. 175 g; diameter stern end: 6.1 cm; diameter at equator: 7.6 cm; diameter at blossom end: 5.5 cm; length base to apex: 7.4 cm.

*Shape*.—Overall: medium oblate, slightly asymmetrical with no mucron tip; base: truncate; apex: depressed; depth of suture: 2.3 mm.

*Skin*.—No pubescence, strong glossiness (nectarine), attractive, lack apparent lenticels; ground color: Yellow Group (13B); blush: Red Group (45A); blush coverage: 78% of surface on average; blush pattern: mottled; adherence of skin to flesh: low, skin is easy to remove.

*Flesh*.—Color: uniform from skin to stone, Yellow-Orange Group (16D), clingstone; uniform non-melting with firm texture. Firmness rating of 8.3 (based on 1 to 10 scale with 10 being very firm) which was comparable to 'Effie' (8.7) and 'Bradley' (8.7). Excellent eating quality, sweet, and mid-acid.

*Pedicel*.—Length: 0.7 cm; diameter: 0.4 cm; color: Yellow-Green Group (144B); strength: moderate to firm, holds on well; fruit stalk cavity depth: 1.4 mm; fruit stalk cavity width: 2.2 mm.

*Ripe date*.—First: July 6 (Julian 187) in west-central Arkansas; similar to 'Bowden' (July 5), 'Effie' ripens ten days later and 'Bradley' ripens 5 days earlier (July 1). Ripening of individual fruit is uniform. Last ripe date: July 16.

*Juice*.—Soluble solids: 13.0%; pH: 4.17; titratable acidity: 0.41% malic acid.

*Storage performance*.—Not evaluated. The instant variety is recommended for home-garden and local market use only.

Pit/stone:

*Size*.—Length 3.8 cm; diameter at midpoint: 2.6 cm; diameter at apex: 1.7 cm.

*Shape*.—Stone shape in lateral view: ovate, asymmetric.

*Color*.—Greyed-Orange Group (167A).

*Tendency of pit to split*.—No split pits most years.

Kernel:

*Size*.—Length 1.9 cm; diameter 1.2 cm.

*Shape*.—Widely elliptic.

*Color*.—Greyed-Orange Group (165B).

*Kernel flavor*.—Bitter.

Uses: Fresh consumption for home-garden or local market use, not evaluated for drying, commercial shipping, or other uses.

The cultivar: The outstanding characteristics of 'A-783CN' are attractive and flavorful white nectarine fruit, bacterial spot resistance, and mid-season ripening compared to other nectarine releases known to the inventors.

We claim:

1. A new and distinct cultivar of nectarine tree named 'A-783CN', substantially as illustrated and described.

* * * * *